United States Patent
Zhang et al.

(10) Patent No.: US 9,351,647 B2
(45) Date of Patent: *May 31, 2016

(54) INDICATION-BASED WORSENING HF ALERT

(71) Applicant: Cardiac Pacemakers, Inc., St. Paul, MN (US)

(72) Inventors: Yi Zhang, Plymouth, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 408 days.

This patent is subject to a terminal disclaimer.

(21) Appl. No.: 13/858,631

(22) Filed: Apr. 8, 2013

(65) Prior Publication Data

US 2013/0226011 A1    Aug. 29, 2013

Related U.S. Application Data

(63) Continuation of application No. 12/561,721, filed on Sep. 17, 2009, now Pat. No. 8,469,898.

(60) Provisional application No. 61/098,526, filed on Sep. 19, 2008.

(51) Int. Cl.
| | |
|---|---|
| *A61B 5/0205* | (2006.01) |
| *A61B 5/00* | (2006.01) |
| *A61B 5/021* | (2006.01) |

(Continued)

(52) U.S. Cl.
CPC ............. *A61B 5/0205* (2013.01); *A61B 5/021* (2013.01); *A61B 5/7275* (2013.01); *A61B 5/7435* (2013.01); *A61B 5/7475* (2013.01); *A61B 5/053* (2013.01); *A61B 5/085* (2013.01); *A61B 5/16* (2013.01)

(58) Field of Classification Search
CPC ..... A61B 5/0205; A61B 5/021; A61B 5/7475
USPC .......................... 600/484, 508, 485, 528, 483
See application file for complete search history.

(56) References Cited

U.S. PATENT DOCUMENTS

| | | | |
|---|---|---|---|
| 6,080,106 | A | 6/2000 | Lloyd et al. |
| 6,454,705 | B1 | 9/2002 | Cosentino et al. |

(Continued)

FOREIGN PATENT DOCUMENTS

| | | |
|---|---|---|
| AU | 2009293198 | 7/2013 |
| EP | 2008581 A2 | 12/2008 |

(Continued)

OTHER PUBLICATIONS

"U.S. Appl. No. 12/561,721, Non Final Office Action mailed Feb. 29, 2012", 8 pgs.

(Continued)

*Primary Examiner* — Catherine Voorhees
*Assistant Examiner* — Roland Dinga
(74) *Attorney, Agent, or Firm* — Schwegman Lundberg & Woessner, P.A.

(57) ABSTRACT

This document discusses, among other things, receiving a user selection of a heart failure symptom, receiving a user selection of an abnormal psychological condition, receiving information about a physiological patient status parameter, and determining a heart failure status using the received information.

20 Claims, 8 Drawing Sheets

(51) Int. Cl.
  *A61B 5/053* (2006.01)
  *A61B 5/085* (2006.01)
  *A61B 5/16* (2006.01)

(56) References Cited

U.S. PATENT DOCUMENTS

| | | | |
|---|---|---|---|
| 6,556,977 | B1 | 4/2003 | Lapointe et al. |
| 6,678,669 | B2 | 1/2004 | Lapointe et al. |
| 6,821,249 | B2 | 11/2004 | Casscells, III et al. |
| 7,127,290 | B2 | 10/2006 | Girouard et al. |
| 7,761,158 | B2 | 7/2010 | Brockway et al. |
| 8,346,360 | B2 | 1/2013 | Libbus et al. |
| 8,369,937 | B2 | 2/2013 | Bardy |
| 8,469,898 | B2 * | 6/2013 | Zhang et al. .......... 600/508 |
| 2003/0055461 | A1 | 3/2003 | Girouard et al. |
| 2003/0083556 | A1 * | 5/2003 | Cosentino et al. .......... 600/300 |
| 2003/0092975 | A1 | 5/2003 | Casscells, III et al. |
| 2004/0034286 | A1 | 2/2004 | Kasper et al. |
| 2004/0122297 | A1 | 6/2004 | Stahmann et al. |
| 2004/0147982 | A1 | 7/2004 | Bardy |
| 2005/0080348 | A1 | 4/2005 | Stahmann et al. |
| 2005/0137481 | A1 | 6/2005 | Sheard et al. |
| 2006/0010090 | A1 | 1/2006 | Brockway et al. |
| 2006/0064030 | A1 | 3/2006 | Cosentino et al. |
| 2006/0116557 | A1 | 6/2006 | Moore et al. |
| 2008/0126124 | A1 | 5/2008 | Schechter |
| 2008/0162182 | A1 | 7/2008 | Cazares et al. |
| 2010/0073170 | A1 | 3/2010 | Siejko et al. |
| 2010/0076321 | A1 | 3/2010 | Zhang et al. |
| 2012/0157856 | A1 | 6/2012 | An et al. |
| 2014/0343438 | A1 | 11/2014 | Sweeney et al. |
| 2014/0343439 | A1 | 11/2014 | Sweeney et al. |

FOREIGN PATENT DOCUMENTS

| | | |
|---|---|---|
| JP | 2006510447 A | 3/2006 |
| JP | 2006510451 A | 3/2006 |
| JP | 2007053436 A | 3/2007 |
| JP | 2007534363 A | 11/2007 |
| JP | 2008053660 A | 3/2008 |
| JP | 2008536607 A | 9/2008 |
| JP | 2009518731 A | 5/2009 |
| JP | 2010514497 A | 5/2010 |
| JP | 2010514498 A | 5/2010 |
| JP | 2012502752 | 2/2012 |
| WO | WO-2010033699 A1 | 3/2010 |
| WO | WO-2014189884 A1 | 11/2014 |

OTHER PUBLICATIONS

"U.S. Appl. No. 12/561,721, Non Final Office Action mailed Oct. 16, 2012", 7 pgs.
"U.S. Appl. No. 12/561,721, Non-Final Office Actions mailed Apr. 29, 2011", 6 pgs.
"U.S. Appl. No. 12/561,721, Notice of Allowance mailed Feb. 22, 2013", 5 pgs.
"U.S. Appl. No. 12/561,721, Response filed Jan. 16, 2013 to Non Final Office Action mailed Oct. 16, 2012", 9 pgs.
"U.S. Appl. No. 12/561,721, Response filed May 22, 2012 to Non Final Office Action mailed Feb. 29, 2012", 9 pgs.
"U.S. Appl. No. 12/561,721, Response filed Aug. 29, 2011 to Non-Final Office Action mailed Apr. 29, 2011", 13 pgs.
"Australian Application Serial No. 2009293198, Office Action mailed May 7, 2012", 3 pgs.
"Australian Application Serial No. 2009293198, Subsequent Examiners Report mailed Dec. 7, 2012", 8 pgs.
"European Application Serial No. 09792660.4, Office Action Response filed Dec. 22, 2011", 14 pgs.
"International Application Serial No. PCT/US2009/057316 International Preliminary Report on Patentability mailed Mar. 31, 2011", 7 pgs.
"International Application Serial No. PCT/US2009/057316, International Search Report mailed Dec. 23, 2009", 5 pgs.
"International Application Serial No. PCT/US2009/057316, Written Opinion mailed Dec. 23, 2009", 8 pgs.
"Japanese Application Serial No. 2011-527959, Office Action mailed Feb. 19, 2013", 3 pgs.
Ekman, I., et al., "Exploring Symptoms in Chronic Heart Failure", The European Journal of Heart Failure, 7, (2005), 699-703.
Ingle, L., et al., "Perception of Symptoms is Out of Proportion to Cardiac Pathology in Patients With "Diastolic Heart Failure"", Heart, 94, (2008), 748-753.
Lavietes, M., et al., "Dyspnea and Symptom Amplification in Asthma", Respiration, 75(2), (2008), 158-162.
Skotzko, C. E., "Symptom Perception in CHF: (why mind matters)", Heart Failure Reviews, [Epub Dec. 11, 2007], (prior to Jun. 13, 2008), 6 pages.
"Australian Application Serial No. 2009293198, Response filed Apr. 2, 2013 to Non Final Office Action dated Nov. 22, 2012", 16.
"Australian Application Serial No. 2009293198, Response filed Oct. 8, 2012 to Non Final Office Action dated May 7, 2012", 18.
"International Application Serial No. PCT/US2014/038719, International Search Report mailed Jul. 21, 2014", 4 pgs.
"International Application Serial No. PCT/US2014/038719, Written Opinion mailed Jul. 2014", 5 pgs.

* cited by examiner

INDICATION-BASED WORSENING HF ALERT

CLAIM OF PRIORITY

This application is a continuation of U.S. patent application Ser. No. 12/561,721, filed on Sep. 17, 2009, now issued as U.S. Pat. No. 8,469,898, which claims the benefit of U.S. Provisional Application No. 61/098,526, filed on Sep. 19, 2008, under 35 U.S.C. § 119(e), each of which are hereby incorporated by reference in its entirety.

BACKGROUND

A body can be thought of as a group of systems working together to maintain a person's health. For example, the circulatory system can be responsible for providing oxygen and nutrients to various organs. The heart can be thought of as the central organ of the circulatory system. The left portions of the heart can draw oxygenated blood from the lungs and supply it to other parts of the body. The body can use the oxygenated blood as part of a metabolic cycle. The metabolic cycle can partially deoxygenate the blood while providing energy to organs or muscle tissue. The right portions of the heart can then return such deoxygenated blood to the lungs where the blood can become oxygenated again.

A variety of physiologic conditions can affect the mechanical or electrical behavior of the heart. A disease such as heart failure ("HF") can reduce the pumping capability or efficiency of the heart. As congestive heart failure progresses, the reduced pumping capability or efficiency of the heart can cause other undesirable symptoms, such as edema (retention of body fluid), weight gain, shortness of breath, poor exercise tolerance, sleeping related problems, or other undesirable symptoms, and can ultimately lead to death.

OVERVIEW

In an example, one or more systems or methods can be used to monitor various physiologic parameters to predict a worsening heart failure status of a patient. A sudden worsening of HF-related signs or symptoms can be referred to as acute heart failure decompensation ("AHFD"). A person having heart failure can sometimes be unaware of such changes in physiologic status. Automatic warning or alert generation systems or methods can assist in early identification of a worsening condition or other significant disease events. Treatment of HF can then be initiated or modified. Treatment can include initiating or modifying pharmacological therapy, using an implantable device (e.g., cardiac resynchronization therapy or one or more other therapies), physiologic monitoring (e.g., through one or more sensors), or the like. Early detection of worsening heart failure can reduce the frequency and the length of hospitalization, improve quality of life, or reduce health care costs.

In certain examples, one or more symptoms or conditions unrelated to heart failure can distort a person's perception of the severity of heart failure-related symptoms. Such distortion can be referred to as heart failure symptom amplification. The present inventors have recognized, among other things, that changing the detection criteria of a method or system to provide an alert for a worsening heart failure condition can be beneficial for persons experiencing symptom amplification.

The present inventors have also recognized that a user interface can be used to obtain information about a person's symptoms or conditions. In certain examples, heart failure status detection criteria can be changed automatically in response to one or more selected symptoms or conditions. In an example, the user interface can be configured to show a clinical indication, such as a disease symptom or physiologic condition to be selected. By selecting a disease symptom or physiologic condition, the user can provide control over heart failure status detection criteria. In certain examples, the user need not have familiarity with technical details about the configuration of one or more sensors or alert generation settings. In an example, the one or more sensors or alert generation settings can be determined automatically in response to the user input. Thus, the user interface can be simplified.

In Example 1, a system includes a user input configured to receive a user selection of a heart failure symptom to indicate whether a heart failure symptom is or has been present, wherein the heart failure symptom includes at least one of dyspnea, edema, or weight change, receive a user selection of an abnormal psychological condition to indicate whether an abnormal psychological condition is or has been present and a heart failure (HF) status processor, coupled to the user input, the HF status processor configured to determine a heart failure status using information about the user selection of the heart failure symptom, information about the user selection of the abnormal psychological condition, and information from a physiological patient status parameter detector.

In Example 2, the heart failure (HF) status indicator of Example 1 is optionally configured to provide a heart failure status indication using information from the HF status processor.

In Example 3, any one or more of the HF status processor of Examples 1 or 2 is optionally configured to controllably adjust at least one of a sensitivity, a specificity, a positive predictive value, or a negative predictive value of the heart failure condition determination using information about the user selections of the heart failure symptom and the abnormal psychological condition.

In Example 4, the abnormal psychological condition of any one or more of Examples 1-3 optionally includes at least one of anxiety, stress, or depression.

In Example 5, the HF status processor of any one or more of Examples 1-4 is optionally configured to increase a likelihood of an indication of a worsening heart failure condition when the user selection indicates that the abnormal psychological condition is or has been present.

In Example 6, the HF status processor of any one or more of Examples 1-5 is optionally configured to detect the heart failure symptom, the abnormal psychological condition, or a heart failure comorbidity using information from the physiological patient status parameter detector without requiring at least one of the user selection of the heart failure symptom, the user selection of the abnormal psychological condition, or a user selection of the heart failure comorbidity.

In Example 7, a method includes receiving a user selection of a heart failure symptom to indicate whether a heart failure symptom is or has been present, wherein the heart failure symptom includes at least one of dyspnea, edema, or weight change, receiving a user selection of an abnormal psychological condition to indicate whether an abnormal psychological condition is or has been present, receiving information about a first physiological patient status parameter, and determining a heart failure status using information about: the user selection of the heart failure symptom, the user selection of the abnormal psychological condition, and the first physiological patient status parameter.

In Example 8, the method of Example 7 optionally includes providing a heart failure status indication using information about the heart failure status.

In Example 9, the determining the heart failure status of any one or more of Example 7 or 8 optionally includes adjusting at least one of a sensitivity, a specificity, a positive predictive value, or a negative predictive value of a worsening heart failure condition determination using information about the user selections of the heart failure symptom and the abnormal psychological condition, optionally includes determining a worsening heart failure condition using information about the first physiological patient status parameter, and the heart failure status indication of any one or more of Example 7 or 8 optionally includes providing the worsening heart failure condition.

In Example 10, the determining the worsening heart failure condition of any one or more of Examples 7-9 optionally includes increasing the sensitivity of the determining when the user selection indicates that the abnormal psychological condition is or has been present.

In Example 11, the abnormal psychological condition of any one or more of Examples 7-10 optionally includes at least one of anxiety, stress, or depression.

In Example 12, the receiving the first physiological patient status parameter of any one or more of Examples 7-11 optionally includes receiving at least one of a heart rate, a respiration rate, a respiration timing, a blood pressure, a lung tidal volume, a physical activity level, a weight, an intrathoracic impedance, a heart sound timing, or a heart sound magnitude.

In Example 13, the receiving the user selection of the heart failure symptom of any one or more of Examples 7-12 optionally includes receiving a user selection indicating that edema is or has been present, the receiving the first physiological patient status parameter of any one or more of Examples 7-12 optionally includes receiving the intrathoracic impedance.

In Example 14, the receiving the user selection of the heart failure symptom of any one or more of Examples 7-13 optionally includes receiving a user selection indicating that dyspnea is or has been present, and the receiving the first physiological patient status parameter of any one or more of Examples 7-13 optionally includes receiving at least one of the respiration rate, the respiration timing, the lung tidal volume, or the physical activity level.

In Example 15, the determining the heart failure status of any one or more of Examples 7-14 optionally includes controllably adjusting the heart failure status determination, the controllably adjusting optionally includes adjusting a first weight for the information about the first physiological patient status parameter relative to a second weight for the information about a different second physiological patient status parameter and using the information obtained from the first and second physiological patient status parameters in conjunction with the first and second weights.

In Example 16, the receiving the user selection of the abnormal psychological condition of any one or more of Examples 7-15 optionally includes receiving a user selection indicating that depression is or has been present and the determining the heart failure status of any one or more of Examples 7-15 optionally includes controllably adjusting the heart failure status determination, the controllably adjusting comprising increasing an effect of respiration-related information on the heart failure status determination in response to the user selection.

In Example 17, the receiving the user selection of the heart failure symptom of any one or more of Examples 7-16 optionally includes receiving a user selection indicating that edema is or has been present and the determining the heart failure status of any one or more of Examples 7-16 optionally includes controllably adjusting the heart failure status determination, the controllably adjusting comprising increasing an effect of intrathoracic impedance information on the heart failure status determination in response to the user selection.

In Example 18, the receiving the user selection of the heart failure symptom of any one or more of Examples 7-17 optionally includes receiving a user selection indicating that dyspnea is or has been present and the determining the heart failure status of any one or more of Examples 7-17 optionally includes controllably adjusting the heart failure status determination, the controllably adjusting comprising increasing an effect of at least one of respiration rate information, respiration timing information, heart rate information, lung tidal volume information, or physical activity level information in response to the user selection.

In Example 19, the method of any one or more of Examples 7-18 optionally includes receiving a user selection of a heart failure (HF) comorbidity to indicate whether an HF comorbidity is or has been present and the determining the heart failure status of any one or more of Examples 7-18 comprises using information about the user selection of the HF comorbidity.

In Example 20, the method of any one or more of Examples 7-19 optionally includes detecting the heart failure symptom, the abnormal psychological condition, or a heart failure comorbidity using information about the first physiological patient status parameter.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
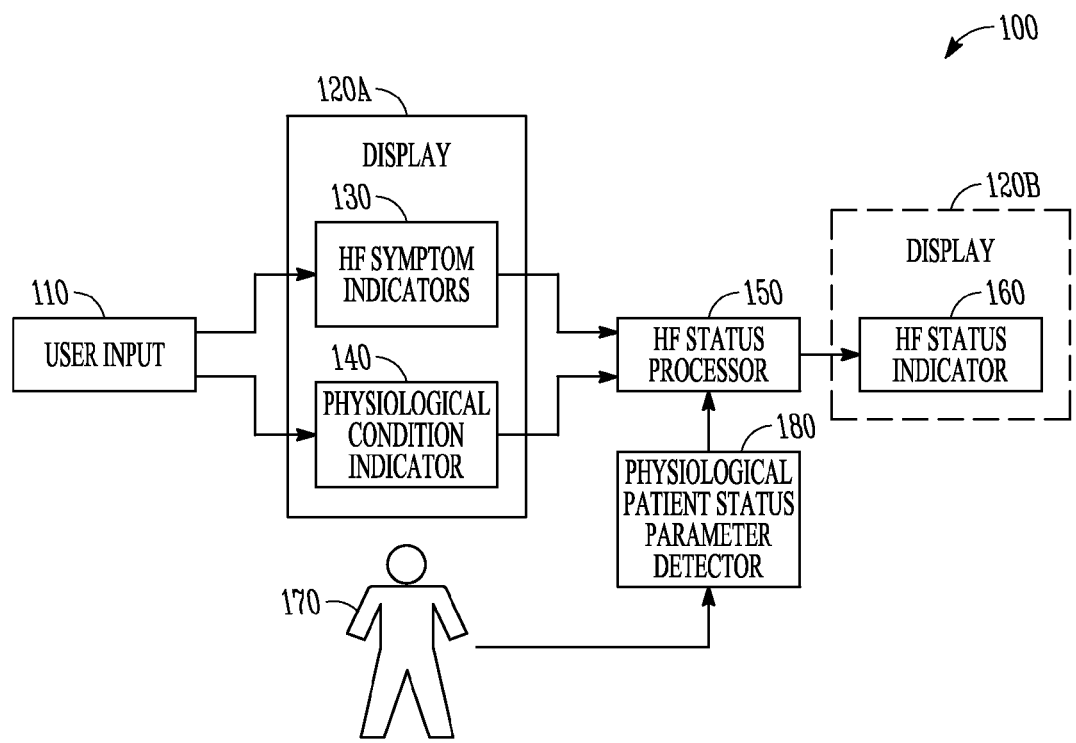
FIG. 1 illustrates generally an example of at least a portion of a system for determining heart failure status.

In certain examples, one or more changes in physiologic patient status parameters can predict the onset or worsening of heart failure. Clinical terms can be used to describe such changes, such as "increasing wetness" (e.g., worsening pulmonary edema, peripheral edema or one or more other forms of edema) or "decreasing exercise tolerance." Physiologic patient status can be derived from information provided by various sensors or by using information provided by a user. In an example, implantable medical devices (IMD's) or external devices can provide one or more sensors. In certain examples, the one or more sensors can include a weight scale, a blood pressure sensor (e.g., a blood pressure cuff or an implantable sensor), an electrocardiogram ("ECG") sensor, an accelerometer, an activity sensor (e.g., an piezoelectric accelerometer, or other sensor), an intrathoracic impedance sensor, an acoustic sensor, a respiration sensor, a blood gas (e.g., oxygen or one or more other gases) sensor, or one or more other sensors.

Examples of information obtained from the one or more sensors can include heart rate, respiration rate, respiration timing, blood pressure, lung tidal volume, physical activity level, exercise tolerance (e.g., a patient's physiologic response to physical activity), weight, intrathoracic impedance (e.g., to asses fluid build-up, to monitor respiration-related parameters, or to monitor cardiac-related parameters), heart sound timing, heart sound magnitude (e.g., an S3 heart sound magnitude), or other information.

In an example, physiologic response to physical activity ("PRA") can be determined by monitoring a patient's physical activity level using an accelerometer, and monitoring a corresponding respiration rate, or heart rate. In an example, an onset of pulmonary edema (e.g., abnormal retention of fluid in the lungs or bronchi) can be derived using information from an intrathoracic impedance sensor.

In certain examples, information (e.g., data) from one or more sensors can be compared with a specified range of values, and when the information meets or exceeds the range, an alert can be generated. Similarly, in certain examples a maximum, minimum, moving average, weighted average, median, mean, or another central tendency of sensor data can be called a "baseline" and compared to a specified range and an alert can be generated when the compared value meets or exceeds the range. In an example, a detected variation of sensor data from a baseline can be used to trigger an alert. In certain examples, a rate of change or trend of sensor data can be compared to a threshold or range and an alert can be generated when the rate of change or trend meets or exceeds the threshold or range.

In certain examples, an alert range for information from a sensor can be specified or modified by a user (e.g., a clinician, a patient, a caregiver, a physician, or one or more others), using a user interface. In certain examples, the user interface can also be used to change, or confirm monitoring parameters (e.g., a sensor configuration) or worsening HF detection criteria. In certain examples, upon confirmation provided via the user interface, an external device (e.g., a portion of a patient monitoring system) or an implantable medical device can be programmed with the modified sensor configuration or alert generation criteria (e.g., worsening HF detection criteria).

Figure 13:
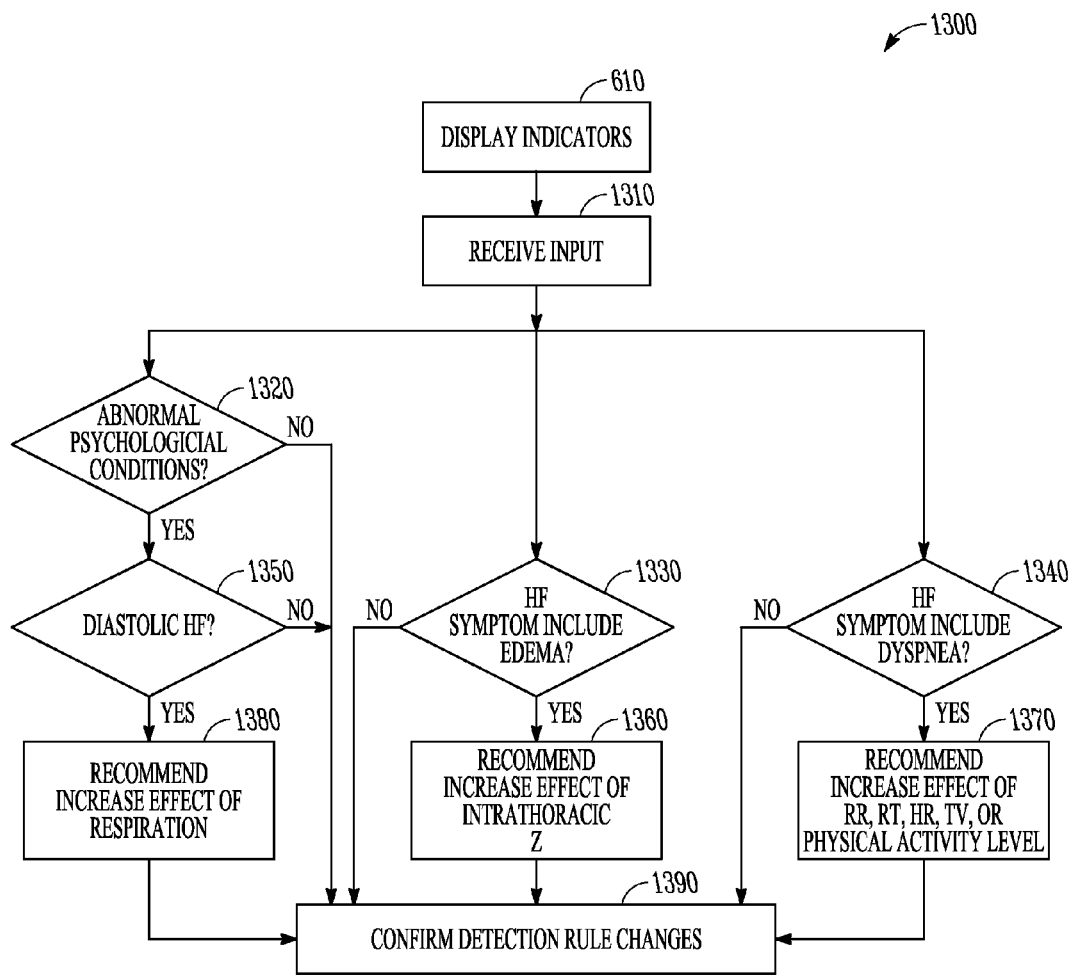
FIG. 13 illustrates generally an example of at least a portion of a method to determine heart failure status including using information obtained from a user.

FIG. 1 illustrates generally an example of at least a portion of system 100 for determining heart failure status. The system 100 can include a user input 110, communicatively coupled to a first display 120A. The first display 120A can include a plurality of user-selectable heart failure symptom indicators 130, and a user-selectable abnormal psychological condition indicator 140. The first display 120A can be communicatively coupled to a heart failure ("HF") status processor 150. The HF status processor 150 can be communicatively coupled to a second display 120B. The second display 120B can include a heart failure ("HF") status indicator 160, and the indicator 160 can be configured to be controllably adjusted by the HF status processor 150, such as a by a heart failure status detection method as shown in FIG. 13. In an example, a person 170 (e.g., a patient) can be communicatively coupled to a physiological patient status parameter detector 180. In certain examples, the physiological patient status parameter detector 180 can be coupled to the HF status processor 150.

In an example, the first display 120A and second display 120B can include the same display (e.g., a single personal computer display). The user input 110 can include a keyboard, mouse, touch-screen or the like. In certain examples, the first display 120A or the user input 110 can be included as a portion of a physician programmer assembly for use in communication with an implantable medical device ("IMD") (e.g., a cardiac rhythm management ("CRM") device), or as a portion of an external patient monitoring assembly (e.g., a bedside monitor located in a person's home).

Figure 2:
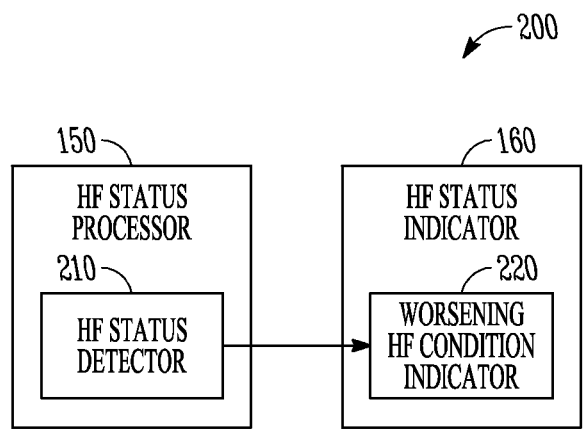
FIG. 2 illustrates generally an example of at least a portion of a system for determining a worsening heart failure including a worsening heart failure condition indicator.

FIG. 2 illustrates generally an example of at least a portion of a system 200 for determining a worsening heart failure condition including an HF status processor 150 and an HF status indicator 160. In this example, the HF status processor 150 can include an HF status detector 210, and the HF status indicator 160 can include a worsening HF condition indicator 220. In an example, the HF status detector 210 can be communicatively coupled to the worsening HF condition indicator 220. In an example, the HF status processor 150 or HF status detector 210 can be included as a portion, part, or component of an IMD, such as a CRM device. In certain examples, the HF status processor 150 or HF status detector 210 can be included as a portion, part, or component of an external assembly, such as a computer server, a personal computer, an external patient monitoring assembly, etc.

Figure 3:
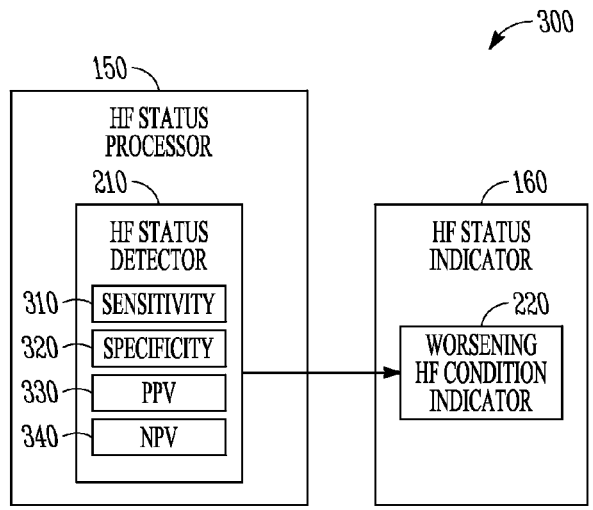
FIG. 3 illustrates generally an example of at least a portion of system including a heart failure status processor configured to control a sensitivity, specificity, positive predictive value, or negative predictive value of a worsening heart failure condition determination.

FIG. 3 illustrates generally an example of at least a portion of system 300 including an HF status processor 150 and an HF status indicator 160. In this example, the HF status processor 150 can include an HF status detector 210 configured to determine a heart failure status, and the HF status indicator 160 can include a worsening HF condition indicator 220 configured to indicate a worsening HF condition. In an example, the HF status processor 150 and HF status detector 210 can be communicatively coupled to the HF status indicator 160 and the worsening HF condition indicator 220.

In an example, the HF status processor 150 can be configured to control at least one of a sensitivity 310, a specificity 320, a positive predictive value 330, or a negative predictive value 340 of a heart failure status determination, such as a worsening heart failure condition determination performed by the HF status detector 210.

The present inventors have recognized, among other things, that one or more tradeoffs can be made between the likelihood of accurately detecting a worsening heart failure condition versus the likelihood of a false alarm. In an example, a sensitivity 310 can be thought of as the likelihood that an actual positive condition can be accurately detected (e.g., a ratio of true positive detection events to the total number of actual positive events). In certain examples, a positive detection event can be thought of as detecting a worsening HF condition (whether or not one actually exists). Increasing a sensitivity 310 can make a detection event more likely. In an example, an increased sensitivity 310 can result in a greater likelihood of declaring a worsening HF condition, even though the underlying likelihood of an actual worsening HF condition has not changed. Generally, a higher sensitivity 310 can result in fewer false negatives at the expense of more false positives.

In certain examples, an alert (e.g., a worsening heart failure condition, an alarm on an individual sensor, an alarm on a patient status parameter, etc.) can be made more sensitive by reducing a threshold value or narrowing an acceptable range of values. In an illustrative example, if a data series (e.g., from a sensor) exhibits a known range of variation, reducing a threshold value can make a threshold crossing more likely. In this example, if the variation can be caused by factors other than the condition of interest, the threshold crossing due to such other factors can also be more likely (e.g., due to noise, comorbidities, malfunction, inherent limits to sensing resolution, or the like). If the threshold crossing occurs due to other factors, it can be referred to as a false positive.

In an example, a specificity 320 can be thought of as the likelihood that an actual negative event results in a negative detection event (e.g., the HF status detector 210 does not detect a condition, and the condition is not occurring or has not occurred). In the example of a worsening heart failure condition determination, a negative detection event can be thought of as not detecting an actual worsening HF condition. A higher specificity 320 can be thought of as more likely to register a true negative detection event, at the expense of more false negative events. Generally, the higher specificity 320 can result in fewer false positives. In an example, the specificity 320 and the sensitivity 310 can be related to, but not dependent on, each other, and a more robust detection scheme can result in both a higher specificity and a higher sensitivity.

In an example, a Positive Predictive Value ("PPV") 330 can be thought of as a ratio of true positive detection events to a total number of positive detection events. In the example of a worsening heart failure condition determination, a higher PPV 330 can be associated with a lower false positive rate. Similarly, a Negative Predictive Value ("NPV") 340 can be thought of as a ratio of true negative detection events to a total number of negative detection events, and a higher NPV 340 can reduce a false negative rate.

Figure 4:
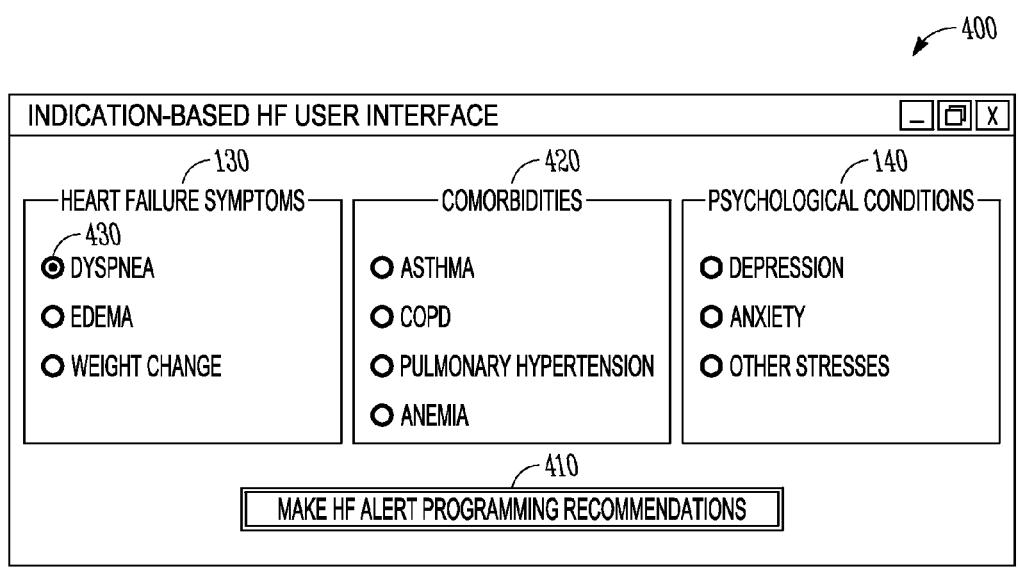
FIG. 4 illustrates generally an example of at least a portion of a user interface included in a system or method for determining heart failure status.

FIG. 4 illustrates generally an example of at least a portion of a user interface 400. In certain examples, the user interface 400 can be included as a portion of a system or method for determining heart failure status. In an example, the user interface 400 can include a user-selectable display of one or more heart failure symptoms 130, of one or more comorbidities 420, and one or more psychological conditions 140.

In the example of FIG. 4, the user-selectable heart failure symptoms 130 can include dyspnea, edema, weight change, or one or more other heart failure symptoms, and one or more radio buttons (e.g., radio button 430) can indicate a user selection. In certain examples, a check-box, list box, or other user-selectable input can be used, (e.g., the selections need not be mutually exclusive). In an example, the radio button 430 can be selected by a user via an input device to a computer (e.g., a keyboard, a mouse, or the like). In an example, the user interface 400 can be provided to a user via telephonic communication (e.g., either by another person, or an automated voice response system), and the user can provide inputs using speech, a touch-tone keypress, or one or more other method.

In certain examples, the user-selectable heart failure symptoms 130 can be further subdivided, or can refer to one or more subcategories. For example, dyspnea can include one or more of dyspnea-on-exertion (e.g., a shortness of breath during physical activity), dyspnea-at-rest, nocturnal paroxysmal dyspnea (e.g., a transient shortness of breath or labored breathing during nighttime, or during sleep), orthopnea (e.g., a shortness of breath or labored breathing depending on whether a person is standing upright or lying down), dyspnea-on-anxiety, or one or more other subdivisions or subcategories of dyspnea. Similarly, in certain examples, other heart failure symptoms, such as edema or weight change, can include one or more of pulmonary edema, generalized edema, peripheral edema, ascites, a positive weight change, a negative weight change, etc.

In the example shown in FIG. 4, the user-selectable comorbidities 420 can include asthma, chronic obstructive pulmonary disease ("COPD"), pulmonary hypertension, anemia, apnea, or one or more other comorbidities. Information about the user selection of the user-selectable comorbidities 420 can be used in the HF status determination. In an example, if a person is experiencing a comorbidity causing a symptom similar to a heart failure symptom, a worsening heart failure status determination can disregard or deemphasize data from one more sensors associated with the comorbidity to avoid a false detection of a worsening heart failure condition.

In an illustrative example, a person can have both asthma and pulmonary edema. In this example, a worsening heart failure status determination can weigh information from an intrathoracic impedance measurement (e.g., to asses fluid build up) more heavily using a first weight than information related to respiration rate or respiration timing using a second weight (e.g., since respiration-related information can be confounded by the asthma). In such an example, the specificity 320 of the worsening heart failure condition determination can be increased.

In the example of FIG. 4, the user-selectable psychological conditions 140 can provide a plurality of abnormal psychological conditions including depression, anxiety, or other stresses or psychological conditions.

In certain examples, the first or second weights can be coefficients used in a numerical calculation, a threshold value, a sensor selection, a gain value (e.g., for a sensor from which physiologic status information can be obtained), a shape of a membership function or coefficient used in a fuzzy logic decision scheme, a coefficient or path through a neural network decision scheme, or the like.

In the example of FIG. 4, after the user has selected one or more of the user-selectable heart failure symptoms 130 (if any), the user-selectable comorbidities 420 (if any), or the user-selectable psychological condition indicators 140 (if any), the user can select a button 410 to "make HF alert programming recommendation." In certain examples, a window can then be displayed on a display showing one or more proposed alert threshold changes (e.g., for an individual sensor or a physiologic patient status alert, for a worsening HF condition alert, or both). In certain examples, the window can show one or more device programming changes, sensor configuration changes, etc., and confirmation or override of the one or more changes can be received via a user input. In an example, a heart failure therapy can be delivered or modified in response to the user selection.

Figure 5:
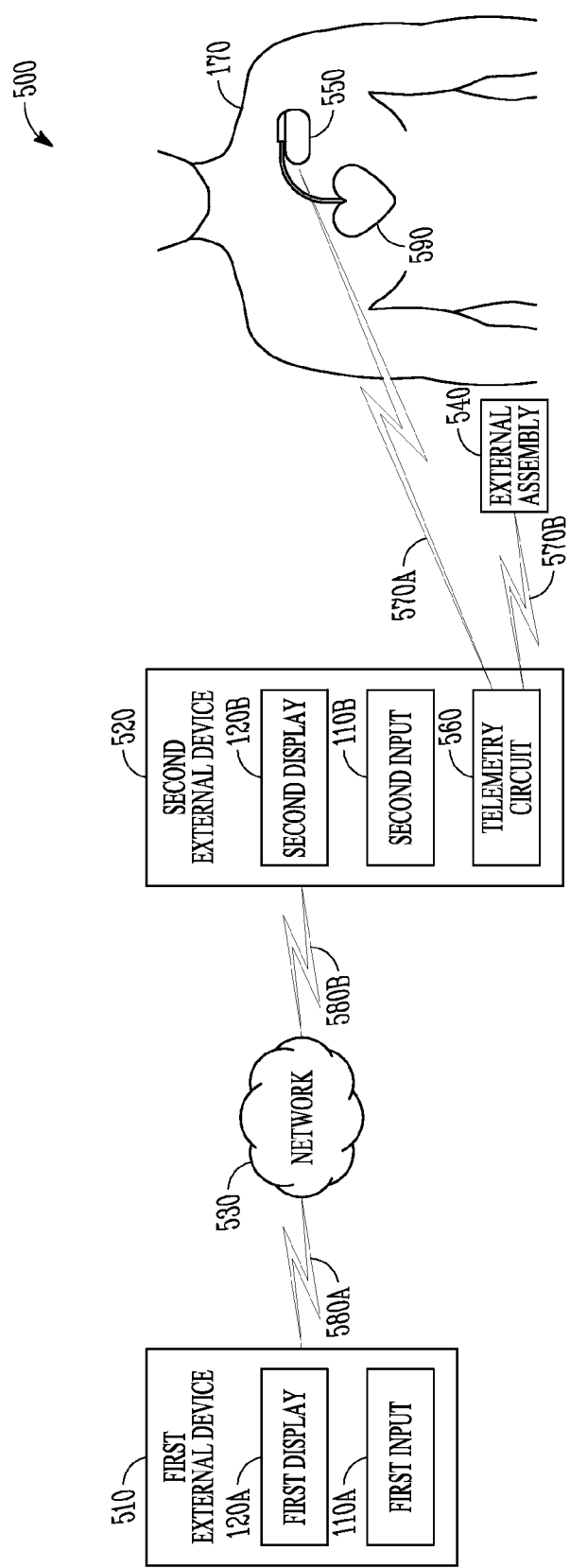
FIG. 5 illustrates generally an example of at least a portion of a system for determining heart failure status including a first external device, a second external device, a network, an implantable sensor assembly, and an external sensor assembly.

FIG. 5 illustrates generally an example of at least a portion of a system 500 for determining heart failure status including a first external device 510, a second external device 520, a network 530, an implantable sensor assembly 550, and an external sensor assembly 540. The first external device 510 can be coupled to the second external device 520 through the network 530 using a first communicative coupling 580A, or a second communicative coupling 580B. In this example, the first external device 510 can include a first display 120A and a first user input 110A. Similarly, the second external device 520 can include a second display 120B and a second input 110B. In certain examples, the second external device 520 can include a telemetry circuit 560 configured to communicatively couple the second external device 520 to the implantable sensor assembly 550 using a first wireless communicative coupling 570A, or to communicatively couple the second external device 520 to the external sensor assembly 540 using a second wireless communicative coupling 570B.

In certain examples, the external sensor assembly 540 can include at least one of a blood pressure sensor, a respiration sensor, a weight scale, or one or more other external sensors. In certain examples, the implantable sensor assembly 550 can include a CRM device implanted within a person 170. The implantable sensor assembly 550 can be coupled to a heart 590 via a lead, and can include cardiac resynchronization therapy delivery circuitry, pacing circuitry, or tachyarrhythmia therapy circuitry (e.g., antitachyarrhythmic pacing or defibrillation shock). In certain examples, the implantable sensor assembly 550 can include one or more of a blood pressure sensor, an intrathoracic impedance sensor, a respiration sensor (e.g., capable of sensing respiration rate, respiration timing, lung tidal volume, minute ventilation, or one or more other respiratory parameters), an acoustic sensor (e.g., to detect heart sounds), an activity level sensor (e.g., an accelerometer or a piezo-electric sensor to detect a person's physical activity, or one or more other activity level sensors), an electrocardiogram sensor, or one or more other implantable sensors. In an example, one or more additional sensor assemblies can be implanted (e.g., an intravascular pressure sensor), and can communicate with either the implantable sensor assembly 550 or with one or more other implantable or external devices. In an example, the second external device 520 can include the external sensor assembly 540, and the wireless coupling 570B can be omitted or replaced by a another wired or wireless coupling.

In an example, the first external device 510 can include a personal computer connected to the network 530 (e.g., for use by a caregiver, a clinician, a patient, a physician, etc., at a convenient location). In certain examples, the second external device 520 can include a physician programmer or a patient monitoring assembly (e.g., a home bed-side monitor, or the like).

Figure 6:
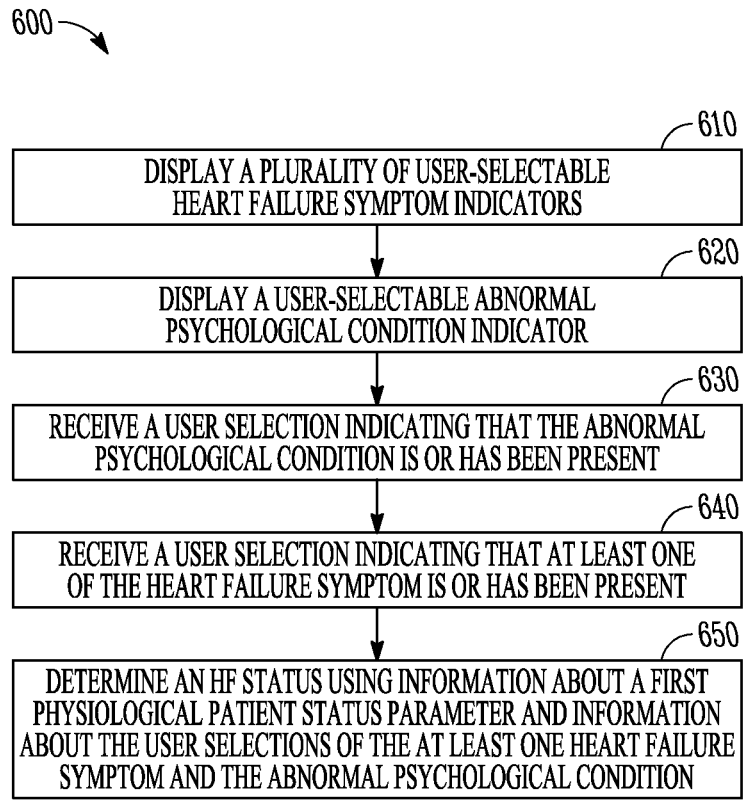
FIG. 6 illustrates generally an example of at least a portion of a method to determine heart failure status using a user input and information obtained from a first physiologic patient status parameter.

FIG. 6 illustrates generally an example of at least a portion of a method 600 to determine heart failure status using a user input and information obtained from a first physiologic patient status parameter. In this example, at 610, one or more heart failure symptoms 130 can be displayed, such as shown in FIG. 4, such as on a first display 120A or a second display 120B. At 620, one or more psychological conditions 140 can be displayed, such as shown in FIG. 4, such as on a first display 120A or a second display 120B. At 630, a user selection can be received indicating that one or more abnormal psychological conditions is or has been present, such as by one or more radio buttons (e.g., radio button 430) or by another user-selectable input (e.g., a check box, list box, or one or more other inputs). At 640, a user selection can be received indicating that at least one heart failure symptom is or has been present, such as by using a radio button 430. In an example, at 640, a user selection can be received indicating that none of the one or more heart failure symptoms displayed at 610 is or have been present. In an example, one or more heart failure comorbidities can be displayed, such as shown in FIG. 4. In this example, a user selection can be received indicating that one or more heart failure comorbidities is or has been present, such as by one or more radio buttons (e.g., radio button 430) or by another user-selectable input (e.g., a check box, list box, or one or more other inputs).

In FIG. 6, at 650, in response to the user selection at 630 and the user selection at 640, an HF status can be determined (e.g., controllably adjusted) using information about the user selection at 630, the user selection at 640, and a first physiological patient status parameter. In an example, in response to the user selection at 630, the user selection at 640, and the user selection of the one or more heart failure comorbidities, an HF status can be determined (e.g., controllably adjusted) using information about the user selection at 630, the user selection at 640, the user selection of the one or more heart failure comorbidities, and a first physiological patient status parameter.

Figure 7:
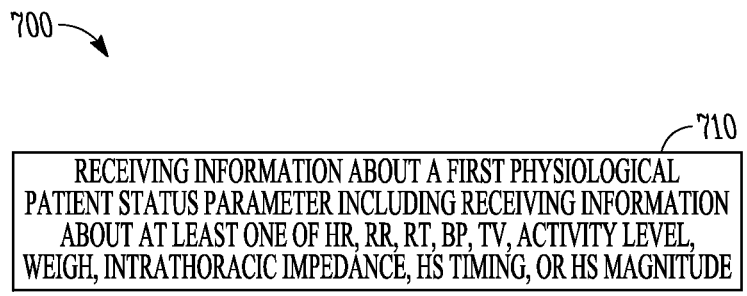
FIG. 7 illustrates generally an example at least a portion of a method to determine heart failure status including deriving information obtained from the first physiologic patient status parameter using at least one of heart rate, respiration rate, respiration timing, blood pressure, lung tidal volume, physical activity level, weight, intrathoracic impedance, heart sound timing, or heart sound magnitude.

FIG. 7 illustrates generally an example at least a portion of a method 700 to determine heart failure status including, at 710, receiving information about a first physiologic patient status parameter including receiving at least one of heart rate ("HR"), respiration rate ("RR"), respiration timing ("RT"), blood pressure ("BP"), lung tidal volume ("TV"), physical activity level, weight, intrathoracic impedance, heart sound ("HS") timing, or HS magnitude. In an example, a first physiologic patient status parameter of wetness or fluid status in relation to an edema symptom can be derived using information from an intrathoracic impedance (e.g., decreasing impedance can indicate fluid retention), a person's weight (e.g., increasing weight can indicate fluid retention), or one or more other sensors.

Figure 8A:
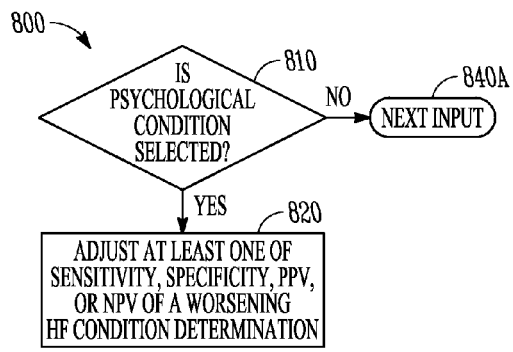
FIG. 8A illustrates generally an example of at least a portion of a method to determine heart failure status including adjusting at least one of a sensitivity, specificity, positive predictive value, or negative predictive value of a worsening heart failure condition determination when a user selects an indicator that an abnormal psychological condition is or has been present.

FIG. 8A illustrates generally an example of at least a portion of a method 800 to determine heart failure status. At 810, if a user selects an indicator 140 that an abnormal psychological condition is or has been present then at 820 at least one of a sensitivity 310, specificity 320, positive predictive value 330, or negative predictive value 340 of a worsening heart failure condition determination can be adjusted. At 810, if a user selects no abnormal psychological condition, then another user input can be processed at 840A.

Figure 8B:
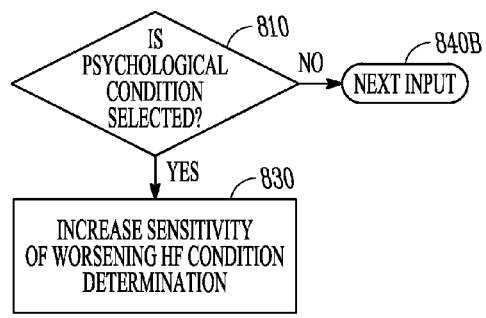
FIG. 8B illustrates generally an example of at least a portion of a method to determine heart failure status including increasing a sensitivity of a worsening heart failure condition determination when a user selects an indicator that an abnormal psychological condition is or has been present.

FIG. 8B illustrates generally an example of at least a portion of a method 800 to determine heart failure status. In this example, at 810, if an abnormal psychological condition is selected then at 830 a sensitivity 310 of a worsening heart failure condition determination can be increased. The present inventors have recognized that for patients suffering from anxiety, stress, depression, or one or more other abnormal psychological conditions, symptom amplification can occur. Such patients can be more likely to want treatment even though an objective severity of their symptoms might be no worse than a patient with no abnormal psychological condition. Hospitalization and follow-up care can be driven by a patient's perception of symptoms. Thus, symptoms can drive therapy decisions for patients, and such symptom amplification can be important from a detection standpoint (e.g., for prediction of impending need for hospitalization). A patient experiencing symptom amplification can be more likely to seek treatment earlier in the heart failure disease progression than a patient without symptom amplification.

In an example, if depression is selected at 810, an alert threshold associated with a respiration-related physiological patient status parameter can be reduced, and can make an alert more likely thus increasing an alert sensitivity. In such an example, a respiration-related parameter can include shortness of breath, poor exercise tolerance, or one or more other physiologic status parameters. In this example, at 810, if a user selects no abnormal psychological condition, then another user input can be processed at 840B.

In an example, a user selection of one or more heart failure comorbidities can be received. In this example, a determination of a status of the one or more heart failure comorbidities can be made. In this example, if a user selects an indicator 140 that an abnormal psychological condition is or has been present then at least one of a sensitivity 310, specificity 320, positive predictive value 330, or negative predictive value 340 of the determination of the status of the one or more heart failure comorbidities can be adjusted.

Figure 9:
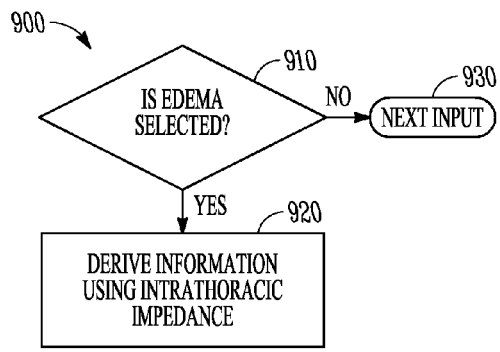
FIG. 9 illustrates generally an example of at least a portion of a method to determine heart failure status including deriving information obtained from a physiological patient status parameter using intrathoracic impedance when a user selects an indicator that edema is or has been present.

FIG. 9 illustrates generally an example of at least a portion of a method to determine heart failure status 900. At 910, if a user selects an indicator that edema (e.g., pulmonary edema) is or has been present, such as on a first display 120A using a first input 110A, or a second display 120B using a second input 110B, then at 920 information about a first physiologic patient status parameter such as wetness can be derived using intrathoracic impedance, or one or more other sensors. In an example, a weight of information derived using intrathoracic impedance, or information derived or received from one or more other sensors, can be increased if edema is selected at 910. In an example, an alert threshold can be established associated with an intrathoracic impedance, and the intrathoracic impedance can be compared with the alert threshold. If the impedance is at or below the threshold, a worsening heart failure condition determination can indicate worsening HF status, or an edema-specific alert can be generated, or both. In an example, one or more existing thresholds associated with the intrathoracic impedance can be increased if edema is selected at 910, making one or more alerts more likely. In FIG. 9, at 910, if edema is not selected, then another user input can be processed at 930. In certain examples, an alert can be displayed by the first external device 510, or the second external device 520, or via an electronic communication (e.g., an electronic mail message, a telephone message, a facsimile ("fax") communication, a user-accessible world wide web application, etc.).

Figure 10:
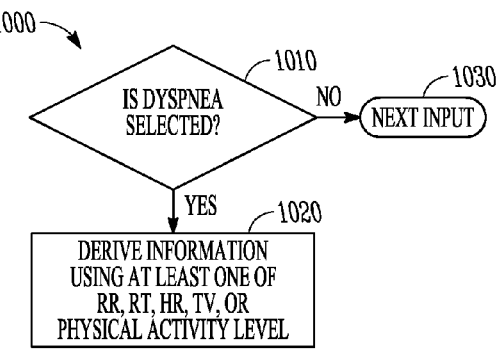
FIG. 10 illustrates generally an example of at least a portion of a method to determine heart failure status including deriving information obtained from a physiological patient status parameter using at least one of respiration rate, lung tidal volume, or physical activity level when a user selects an indicator that dyspnea is or has been present.

FIG. 10 illustrates generally an example of at least a portion of a method to determine heart failure status 1000. In this example, at 1010, if a user selects that dyspnea is or has been present, such as on a first display 120A using a first input 110A, or a second display 120B using a second input 110B, then at 1020 information about a first physiologic patient status parameter such as shortness of breath or exercise tolerance can be derived using information obtained using at least one of respiration rate, respiration timing, heart rate, lung tidal volume, physical activity level, or one or more other sensors. In an example, a weight of information derived using at least one of respiration rate, respiration timing, heart rate, lung tidal volume, physical activity level, or information derived or received from one or more other sensors, can be increased if dyspnea is selected at 1010. In an example, an exercise tolerance can be evaluated by using information about heart rate and physical activity level, or respiration rate and physical activity level, or one or more other sensors. In an example, an excessive heart rate combined with a relatively moderate physical activity level can indicate poor exercise tolerance. In FIG. 10, at 1010, if dyspnea is not selected, then another user input can be processed at 1030.

Figure 11:
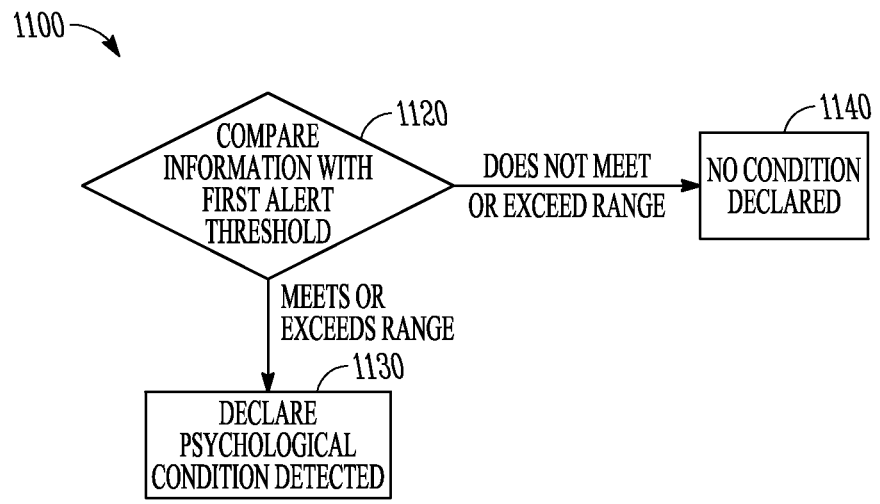
FIG. 11 illustrates generally an example of at least a portion of a method to determine heart failure status including comparing information obtained from a physiological patient status parameter with a first alert threshold or range.

FIG. 11 illustrates generally an example of at least a portion of a method to determine heart failure status 1100. In certain examples, one or more physiological patient status parameters can be used to detect one or more abnormal psychological conditions in addition to or instead of using a user selection. At 1120, information obtained from a first physiological patient status parameter can be compared with a first alert threshold or range. At 1130, if the first physiological patient status parameter meets or exceeds the threshold, or is outside the range, then an abnormal psychological condition can be declared as detected (e.g., without requiring a user selection of the abnormal psychological condition). In an example, an alert or warning can be generated. In FIG. 11, at 1120, if the comparison of the information with the first alert threshold fails to meet or exceed the threshold, then at 1140 the one or more abnormal psychological conditions need not be declared as detected.

Figure 12:
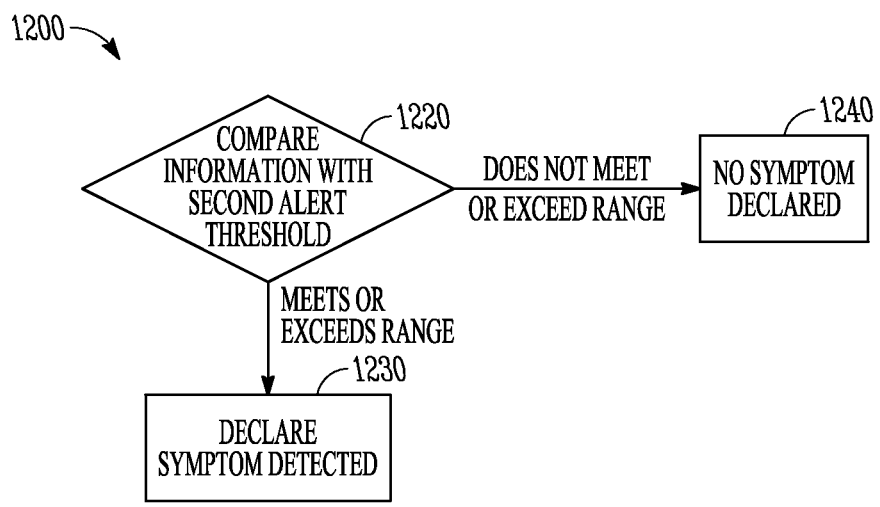
FIG. 12 illustrates generally an example of at least a portion of a method to determine heart failure status including comparing information obtained from a physiological patient status parameter with a second alert threshold or range.

FIG. 12 illustrates generally an example of at least a portion of a method to determine heart failure status 1200. In certain examples, one or more physiologic patient status parameters can be used to detect one or more HF symptoms in addition to or instead of using a user selection. At 1220, information obtained from a first physiological patient status parameter can be compared with a second alert threshold or range. At 1230, if the first physiological patient status parameter meets or exceeds the threshold, or is outside the range, then the one or more HF symptoms can be declared as detected (e.g., without requiring a user selection of the one or more symptoms). In an illustrative example, a lower threshold for intrathoracic impedance, or one or more other sensors, can be established. In this example, if an intrathoracic impedance is decreasing, such information can be used to determine that a physiologic patient status of wetness can be increasing. If wetness increases such that it meets or exceeds a threshold, then the heart failure symptom of edema can be declared as detected. In FIG. 12, at 1220, if the comparison of the information with the second alert threshold fails to meet or exceed the threshold, or is not outside the range, then at 1240 the one or more heart failure symptoms need not be declared as detected.

FIG. 13 illustrates generally an example of at least a portion of method to determine heart failure status 1300. At 610, user-selectable indicators are displayed, such as those shown in the user interface of FIG. 4. At 1310, user input can be received such as by using a first display 120A and a first user input 110A, or a second display 120B and a second user input 110B. At 1320, if an input indicates that one or more abnormal psychological conditions is or have been present, or one or more abnormal psychological conditions have been detected, then a second test can be performed at 1350. In FIG. 13, at 1350, if a user input is of a diastolic heart failure condition, or if a diastolic heart failure condition can be detected, then at 1380 a recommendation can be made to increase an effect of respiration-related information on the heart failure status determination. Diastolic heart failure can occur when heart tissue cannot relax normally during diastole. Diastole can be thought of as the resting phase of the heart's pumping cycle. Such an abnormal lack of relaxation can diminish the heart's ability to properly re-fill with blood, reducing the heart's ability to pump an adequate amount of blood (e.g., hemodynamic insufficiency). Diastolic heart failure, coupled with one or more abnormal psychological conditions, can result in amplified respiratory symptoms or one or more other symptoms.

In certain examples, increasing an effect of respiration-related information can include changing an alert threshold or alert range associated with at least one sensor to increase a sensitivity 310 of the alert. In certain examples, increasing an effect of respiration-related information can include increasing a weight of information derived from one or more respiration-related sensors with respect to one or more non-respiration-related sensors. Respiration-related information can include one or more of respiration rate information, respiration timing information, lung tidal volume information, physiologic patient status parameters such as shortness of breath, exercise tolerance (e.g., a physiologic response to physical activity), or information derived from one or more other sensors. Respiration-related information can also include one or more derived parameters, determined using information from one or more sensors, such as minute ventilation (e.g., a volume in liters exhaled by a person during a minute), or one or more other parameters.

At 1330, if a user input is received indicating that edema is or has been present, or if edema has been detected, then at 1360 a recommendation can be made to increase an effect of an intrathoracic impedance information, or information from one or more other sensors, on the HF status indicator. In an example, increasing an effect of intrathoracic impedance information can include reducing an alert threshold or narrowing an acceptable range associated with an intrathoracic impedance sensor, or increasing a weight of information from intrathoracic impedance sensor with respect to one or more other sensors. Intrathoracic impedance-related information can also be derived from a physiologic patient status parameter such as wetness, or one or more other physiologic patient status parameters.

At 1340, if a user input is received indicating that dyspnea is or has been present, or if dyspnea has been detected, then at 1370 a recommendation can be made to increase an effect of one or more of information related to respiration rate, respiration timing, heart rate, lung tidal volume or physical activity level, information derived from a combination (e.g., minute ventilation), or a physiologic patient status parameter such as shortness of breath.

At 1390, one or more of a recommendation at 1380, a recommendation at 1360, or a recommendation at 1370 can be confirmed by a user. In certain examples, in response to a user confirmation, a worsening heart failure condition determination or one or more other individual alerts can be updated.

In certain examples, one or more of the method examples can be implemented as a portion of the heart failure status processor 150. In certain examples, some or all of the HF status processor 150 can be included as a portion, part, or component of the first external device 510, the second external device 520, the implantable sensor assembly 550, or the external sensor assembly 540.

In an example, if a user input is received indicating that one or more heart failure comorbidities is or have been present, then a recommendation can be made to adjust (e.g., increase or decrease, or otherwise modify) an effect one or more physiologic patient status parameters related to the one or more user-selected heart failure comorbidities.

Figure 14:
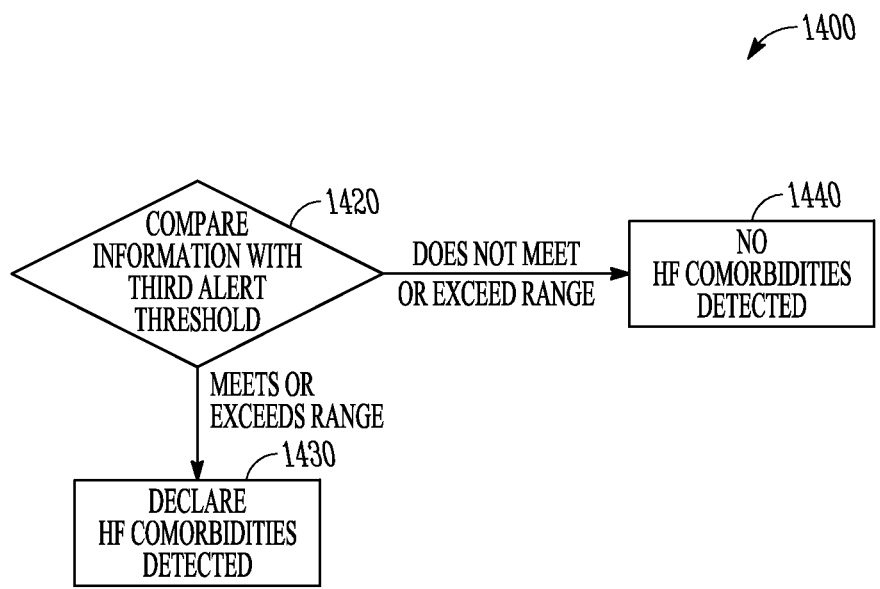
FIG. 14 illustrates generally an example of at least a portion of a method to determine heart failure status including comparing information obtained from a physiological patient status parameter with a third alert threshold or range.

FIG. 14 illustrates generally an example of at least a portion of a method to determine heart failure status 1400. In certain examples, one or more physiological patient status parameters can be used to detect one or more heart failure comorbidities in addition to or instead of using a user selection. At 1420, information obtained from a first physiological patient status parameter can be compared with a third alert threshold or range. At 1430, if the first physiological patient status parameter meets or exceeds the threshold, or is outside the range, then one or more heart failure comorbidities can be declared as detected (e.g., without requiring a user selection of the abnormal psychological condition). In an example, an alert or warning can be generated. In FIG. 14, at 1420, if the comparison of the information with the third alert threshold fails to meet or exceed the threshold, then at 1440 the one or more heart failure comorbidities need not be declared as detected.

In an example, a worsening HF status determination can be made based on the one or more abnormal psychological conditions declared at 1130 as shown in FIG. 11, the one or more HF symptoms declared at 1230 as shown in FIG. 12, or the one or more heart failure comborbidities declared at 1430, as if one or more of the detected abnormal psychological conditions, HF symptoms, or heart failure comorbidities had been selected by a user. In such an example, a worsening HF status determination can automatically compensate for an onset of one or more of depression or another abnormal psychological condition, one or more heart failure symptoms, or one or more heart failure comorbidities. In certain examples, programming changes prompted by such automatic compensation to a worsening HF status determination, or to one or more monitoring parameters associated with one or more sensors, can be overridden or modified by a user, such as during a verification process.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), or the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system, comprising:
  a user input configured to:
    receive a user selection of a heart failure symptom to indicate whether a heart failure symptom is or has been present, wherein the heart failure symptom includes at least one of dyspnea, edema, or weight change; and
    receive a user selection of a heart failure (HF) comorbidity to indicate whether an HF comorbidity is or has been present; and
  a heart failure (HF) status processor, coupled to the user input, the HF status processor configured to determine a heart failure status using information about the user selection of the heart failure symptom and information received from a physiological patient status parameter detector, the information received from the physiological patient status parameter detector including information about a first physiological patient status parameter and a different second physiological patient status parameter;
  wherein the HF status processor configured to determine the heart failure status is further configured to controllably adjust the heart failure status determination, wherein controllably adjusting the heart failure status determination comprises:
    adjusting a first weight for the information about the first physiological patient status parameter relative to a second weight for the information about the different second physiological patient status parameter; and
    using the information obtained from the first and second physiological patient status parameters in conjunction with the first and second weights.

2. The system of claim 1, comprising a heart failure (HF) status indicator configured to provide a heart failure status indication using information from the HF status processor.

3. The system of claim 2, wherein the HF status processor is configured to controllably adjust at least one of a sensitivity, a specificity, a positive predictive value, or a negative predictive value of the heart failure condition determination using information about the user selection of the heart failure symptom.

4. The system of claim 1, wherein the first physiological patient status parameter includes at least one of a heart rate, a respiration rate, a respiration timing, a blood pressure, a lung tidal volume, a physical activity level, a weight, an intrathoracic impedance, a heart sound timing, or a heart sound magnitude.

5. The system of claim 4, wherein the user input configured to receive the heart failure symptom indicator is further configured to receive an indication that edema is or has been present; and
  wherein the physiological patient status parameter includes the intrathoracic impedance.

6. The system of claim 4, wherein the user input configured to receive the heart failure symptom indicator is further configured to receive an indication that dyspnea is or has been present; and
  wherein the first physiological patient status parameter includes at least one of the respiration rate, the respiration timing, the lung tidal volume, or the physical activity level.

7. A method, comprising:
  receiving a heart failure symptom indicator that indicates whether a heart failure symptom is or has been present, wherein the heart failure symptom includes at least one of dyspnea, edema, or weight change;
  receiving a heart failure (HF) comorbidity indicator that indicates whether an HF comorbidity is or has been present;
  receiving information about a first physiological patient status parameter; and
  determining a heart failure status using information about:
    the heart failure symptom;
    the HF comorbidity; and
    the first physiological patient status parameter, wherein the determining the heart failure status includes controllably adjusting the heart failure status determination, the controllably adjusting comprising:
adjusting a first weight for the information about the first physiological patient status parameter relative to a second weight for the information about a different second physiological patient status parameter; and
using the information obtained from the first and second physiological patient status parameters in conjunction with the first and second weights.

8. The method of claim 7, comprising providing a heart failure status indication using information about the heart failure status.

9. The method of claim 7, comprising:
wherein the determining the heart failure status comprises:
adjusting at least one of a sensitivity, a specificity, a positive predictive value, or a negative predictive value of a worsening heart failure condition determination using information about the heart failure symptom indicator; and
determining a worsening heart failure condition using information about the first physiological patient status parameter; and
wherein the providing the heart failure status indication includes providing the worsening heart failure condition.

10. The method of claim 7, wherein the receiving the first physiological patient status parameter includes receiving at least one of a heart rate, a respiration rate, a respiration timing, a blood pressure, a lung tidal volume, a physical activity level, a weight, an intrathoracic impedance, a heart sound timing, or a heart sound magnitude.

11. The method of claim 10, wherein the receiving the heart failure symptom indicator includes receiving an indication that edema is or has been present; and
wherein the receiving the first physiological patient status parameter includes receiving the intrathoracic impedance.

12. The method of claim 10, wherein the receiving the heart failure symptom indicator includes receiving an indication that dyspnea is or has been present; and
wherein the receiving the first physiological patient status parameter includes receiving at least one of the respiration rate, the respiration timing, the lung tidal volume, or the physical activity level.

13. The method of claim 7, wherein the receiving the abnormal psychological condition includes receiving an indication that depression is or has been present; and
wherein the determining the heart failure status includes controllably adjusting the heart failure status determination, the controllably adjusting comprising increasing an effect of respiration-related information on the heart failure status determination in response to receiving the indication that depression is or has been present.

14. The method of claim 7, wherein the receiving the heart failure symptom indicator includes receiving an indication that edema is or has been present; and
wherein the determining the heart failure status includes controllably adjusting the heart failure status determination, the controllably adjusting comprising increasing an effect of intrathoracic impedance information on the heart failure status determination in response to receiving the indication that edema is or has been present.

15. The method of claim 7, wherein the receiving the heart failure symptom indicator includes receiving an indication that dyspnea is or has been present; and
wherein the determining the heart failure status includes controllably adjusting the heart failure status determination, the controllably adjusting comprising increasing an effect of at least one of respiration rate information, respiration timing information, heart rate information, lung tidal volume information, or physical activity level information in response to receiving the indication that dyspnea is or has been present.

16. The method of claim 7, further comprising:
detecting at least one of the heart failure symptom and a heart failure comorbidity using information about the first physiological patient status parameter.

17. A system, comprising:
an assembly configured to:
receive a heart failure symptom indicator that indicates whether a heart failure symptom is or has been present, wherein the heart failure symptom includes at least one of dyspnea, edema, or weight change; and
receive a heart failure (HF) comorbidity indicator that indicates whether an HF comorbidity is or has been present; and
a heart failure (HF) status processor, coupled to the assembly, the HF status processor configured to determine a heart failure status using information about the heart failure symptom indicator and information received from a physiological patient status parameter detector, the information received from the physiological patient status parameter detector including information about a first physiological patient status parameter and a different second physiological patient status parameter;
wherein the HF status processor configured to determine the heart failure status is further configured to controllably adjust the heart failure status determination, wherein controllably adjusting the heart failure status determination comprises:
adjusting a first weight for the information about the first physiological patient status parameter relative to a second weight for the information about the different second physiological patient status parameter; and
using the information obtained from the first and second physiological patient status parameters in conjunction with the first and second weights.

18. The system of claim 17, further comprising a heart failure (HF) status indicator configured to provide a heart failure status indication using information from the HF status processor.

19. The system of claim 18, wherein the HF status processor is configured to controllably adjust at least one of a sensitivity, a specificity, a positive predictive value, or a negative predictive value of the heart failure condition determination using information about the heart failure symptom.

20. The system of claim 17, wherein the first physiological patient status parameter includes at least one of a heart rate, a respiration rate, a respiration timing, a blood pressure, a lung tidal volume, a physical activity level, a weight, an intrathoracic impedance, a heart sound timing, or a heart sound magnitude.

* * * * *